(12) United States Patent
Moody et al.

(10) Patent No.: US 8,614,335 B2
(45) Date of Patent: Dec. 24, 2013

(54) PROCESS AND INTERMEDIATES USEFUL IN THE PREPARATION OF STATINS, PARTICULARLY ATORVASTATIN

(75) Inventors: David John Moody, Fife (GB); Jonathan William Wiffen, Craigavon (GB)

(73) Assignee: Redx Pharma Limited, Manchester (GB)

( * ) Notice: Subject to any disclaimer, the term of this patent is extended or adjusted under 35 U.S.C. 154(b) by 558 days.

(21) Appl. No.: 12/191,518

(22) Filed: Aug. 14, 2008

(65) Prior Publication Data

US 2009/0062553 A1 Mar. 5, 2009

Related U.S. Application Data

(62) Division of application No. 10/563,459, filed as application No. PCT/GB2004/003206 on Jul. 23, 2004, now Pat. No. 7,414,141.

(30) Foreign Application Priority Data

Jul. 25, 2003 (GB) .................................. 0317393.7
Mar. 26, 2004 (GB) .................................. 0406760.9

(51) Int. Cl.
  *C07D 207/34* (2006.01)
  *C07D 309/10* (2006.01)
  *C07D 309/30* (2006.01)
  *C07D 405/06* (2006.01)

(52) U.S. Cl.
  USPC .............................. 548/517; 548/562; 549/419

(58) Field of Classification Search
  None
  See application file for complete search history.

(56) References Cited

U.S. PATENT DOCUMENTS 5,385,929 A * 1/1995 Bjorge et al. .................. 514/422

FOREIGN PATENT DOCUMENTS

EP 0409281 A1 1/1991
WO WO-89/07598 A2 8/1989

(Continued)

OTHER PUBLICATIONS

Harden, A. et al., "The chemical action of *Bacillus coli communis* and similar organisms on carbohydrates and allied compounds," J. of the Chemical Society, Transactions, 79:610-628 (1901) Abstract Only.

(Continued)

*Primary Examiner* — Sun Jae Loewe

(74) *Attorney, Agent, or Firm* — Alan W. Steele; Foley Hoag LLP

(57) ABSTRACT

There is provided a process for the preparation of a compound of formula (7) or salts thereof: wherein $R^1$ represents a hydrogen or a hydrocarbyl group, $R^2$ represents a hydrogen or substituent group, $R^3$ represents a hydrogen or a hydrocarbyl group, and X represents a hydrogen or substituent group which comprises a) cyanating a compound of formula (1): wherein Y represents a halo group, preferably Cl or Br; $P^1$ represents hydrogen or a protecting group, and W represents =O or $-OP^2$, in which $P^2$ represents hydrogen or a protecting group, to give a compound of formula (2): b) reducing the compound of formula (2) to give a compound of formula (3): coupling the compound of formula (3) with a compound of formula (4): to give a compound of formula (5): when W represents $-OP^2$, deprotecting and then oxidizing the compound of formula (5) to give a compound of formula (6): and e) subjecting the compound of formula (5) when W represents =O, or compound of formula (6) to ring-opening, and removal of any remaining protecting groups, to give a compound of formula (7) or salts thereof.

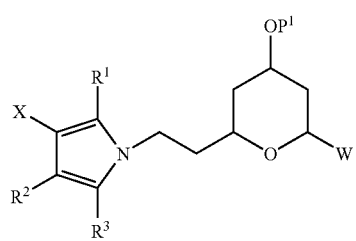
(5)
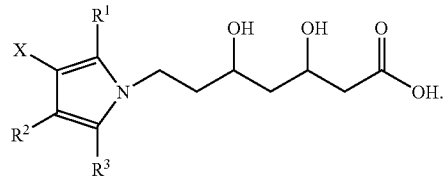
(7)
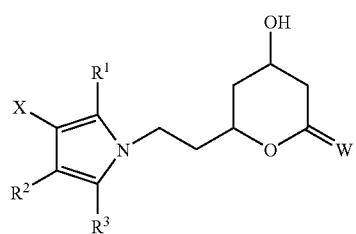
(6)
15 Claims, No Drawings

(56) References Cited

FOREIGN PATENT DOCUMENTS

| WO | WO-92/06968 A1 | 4/1992 |
|----|----------------|--------|
| WO | WO-94/20492 A1 | 9/1994 |
| WO | WO-03/016317 A1 | 2/2003 |
| WO | WO-2004/005250 A1 | 1/2004 |
| WO | WO-2004/027075 A2 | 4/2004 |
| WO | WO-2004/089894 A1 | 10/2004 |
| WO | WO-2004/096788 A1 | 11/2004 |

OTHER PUBLICATIONS

Tararov, V.I. et al., "Synthesis of the Chiral Side Chain of Statins—Lactone versus Lactol Pathway," Eur. J. Org. Chem., 5543-5550 (2006).

International Search Report dated Dec. 30, 2004 for PCT/GB2004/003206.

* cited by examiner

PROCESS AND INTERMEDIATES USEFUL IN THE PREPARATION OF STATINS, PARTICULARLY ATORVASTATIN

RELATED APPLICATIONS

This application is a divisional of U.S. patent application Ser. No. 10/563,459, filed Jan. 4, 2006, now U.S. Pat. No. 7,414,141; which claims the benefit of priority to Patent Cooperation Treaty Application number PCT/GB2004/003206, filed Jul. 23, 2004; which claims the benefit of priority to Great Britain Patent Application serial number 0406760.9, filed Mar. 26, 2004; and Great Britain Patent Application serial number 0317393.7, filed Jul. 25, 2003. The entirety of each of them is hereby incorporated by reference.

The present invention concerns a process and intermediate compounds useful in the preparation of statins, particularly atorvastatin.

According to the present invention, there is provided a process for the preparation of a compound of formula (7) or salts thereof:

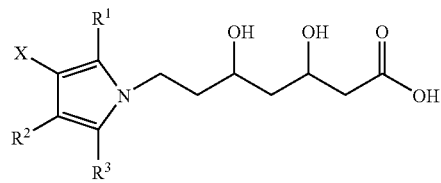

wherein
$R^1$ represents a hydrogen or a hydrocarbyl group
$R^2$ represents a hydrogen or substituent group
$R^3$ represents a hydrogen or a hydrocarbyl group
X represents a hydrogen or substituent group
which comprises
a) cyanating a compound of formula (1):

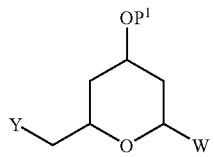

wherein Y represents a halo group, preferably Cl or Br; $P^1$ represents hydrogen or a protecting group, and W represents —O or —$OP^2$, in which $P^2$ represents hydrogen or a protecting group,
to give a compound of formula (2):

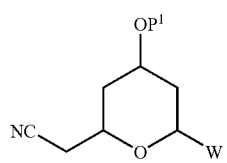

b) reducing the compound of formula (2) to give a compound of formula (3):

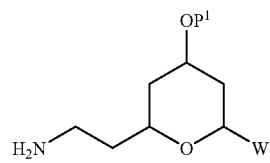

c) coupling the compound of formula (3) with a compound of formula (4):

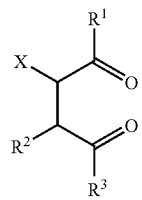

to give a compound of formula (5):

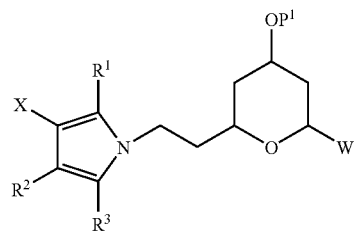

d) when W represents —$OP^2$, deprotecting and then oxidising the compound of formula (5) to give a compound of formula (6):

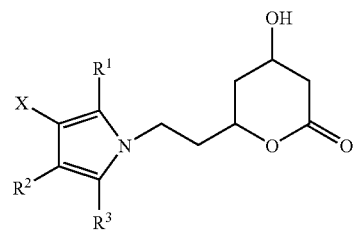

and
e) subjecting the compound of formula (5) when W represents =O, or compound of formula (6) to ring-opening, and removal of any remaining protecting groups, to give a compound of formula (7) or salts thereof:

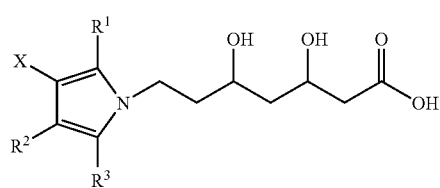

Hydrocarbyl groups which may be represented by $R^1$ and $R^3$ independently include alkyl, alkenyl and aryl groups, and any combination thereof, such as aralkyl and alkaryl, for example benzyl groups.

Alkyl groups which may be represented by $R^1$ and $R^3$ include linear and branched alkyl groups comprising up to 20 carbon atoms, particularly from 1 to 7 carbon atoms and preferably from 1 to 5 carbon atoms. When the alkyl groups are branched, the groups often comprising up to 10 branch chain carbon atoms, preferably up to 4 branch chain atoms. In certain embodiments, the alkyl group may be cyclic, commonly comprising from 3 to 10 carbon atoms in the largest ring and optionally featuring one or more bridging rings. Examples of alkyl groups which may be represented by $R^1$ and $R^3$ include methyl, ethyl, propyl, 2-propyl, butyl, 2-butyl, t-butyl and cyclohexyl groups.

Alkenyl groups which may be represented by $R^1$ and $R^3$ include $C_{2-20}$, and preferably $C_{2-6}$ alkenyl groups. One or more carbon-carbon double bonds may be present. The alkenyl group may carry one or more substituents, particularly phenyl substituents. Examples of alkenyl groups include vinyl, styryl and indenyl groups.

Aryl groups which may be represented by $R^1$ and $R^3$ may contain 1 ring or 2 or more fused rings which may include cycloalkyl, aryl or heterocyclic rings. Examples of aryl groups which may be represented by $R^1$ and $R^3$ include phenyl, tolyl, fluorophenyl, chlorophenyl, bromophenyl, trifluoromethylphenyl, anisyl, naphthyl and ferrocenyl groups.

When any of $R^1$ and $R^3$ is a substituted hydrocarbyl group, the substituent(s) should be such so as not to adversely affect the rate or selectivity of any of the reaction steps or the overall process. Optional substituents include halogen, cyano, nitro, hydroxy, amino, thiol, acyl, hydrocarbyl, heterocyclyl, hydrocarbyloxy, mono or di-hydrocarbylamino, hydrocarbylthio, esters, carbamates, carbonates, amides, sulphonyl and sulphonamido groups wherein the hydrocarbyl groups are as defined for $R^1$ above. One or more substituents may be present. Examples of $R^1$ or $R^3$ groups having more than one substituent present include —$CF_3$ and —$C_2F_5$.

Substituent groups which may be represented by X and $R^2$ independently include hydrocarbyl groups as defined above for $R^1$, electron donating groups, electron withdrawing groups, halogens and heterocyclic groups. Substituent groups are commonly selected from the group consisting of optionally substituted alkoxy (preferably $C_{1-4}$-alkoxy), optionally substituted aryl (preferably phenyl), optionally substituted aryloxy (preferably phenoxy), polyalkylene oxide (preferably polyethylene oxide or polypropylene oxide), carboxy, phosphato, sulpho, nitro, cyano, halo, ureido, —$SO_2F$, hydroxy, ester, —$NR^aR^b$, —$COR^a$, —$CONR^aR^b$, —NH-$COR^a$, —$OCONR^aR^b$, carboxyester, sulphone, and $SO_2NR^aR^b$ wherein $R^a$ and $R^b$ are each independently H, optionally substituted aryl, especially phenyl, or optionally substituted alkyl (especially $C_{1-4}$-alkyl) or, in the case of —$NR^aR^b$, —$CONR^aR^b$, —$OCONR^aR^b$ and —$SO_2NR^aR^b$, $R^a$ and $R^b$ may also together with the nitrogen atom to which they are attached represent an aliphatic or aromatic ring system; or a combination thereof.

Preferably, there is provided a process for the preparation of a compound of formula (7) or salts thereof:

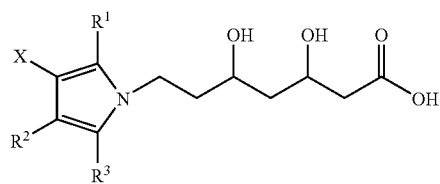

wherein $R^1$ represents an alkyl group, such as a $C_{1-6}$ alkyl group, and preferably an isopropyl group $R^2$ represents an aryl group, preferably a phenyl group $R^3$ represents an aryl group, preferably a 4-fluorophenyl group X represents a group of formula —COZ, wherein Z represents —$OR^4$, in which $R^4$ represents an alkyl, preferably a methyl or ethyl, group, or —$NR^5R^6$, wherein $R^5$ and $R^6$ each independently represent H, alkyl, or aryl, and preferably $R^5$ is H and $R^6$ is phenyl which comprises a) cyanating a compound of formula (1):

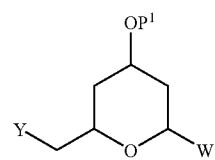

wherein Y represents a halo group, preferably Cl or Br; $P^1$ represents hydrogen or a protecting group, and W represents =O or —$OP^2$, in which $P^2$ represents hydrogen or a protecting group, to give a compound of formula (2):

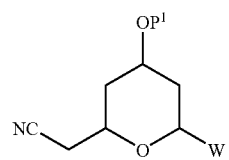

b) reducing the compound of formula (2) to give a compound of formula (3):

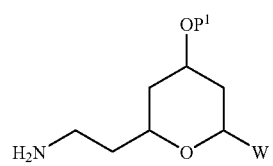

c) coupling the compound of formula (3) with a compound of formula (4):

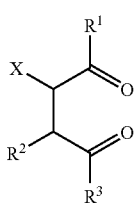

to give a compound of formula (5):

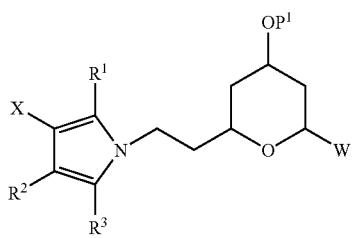

d) when W represents —OP², deprotecting and then oxidising the compound of formula (5) to give a compound of formula (6):

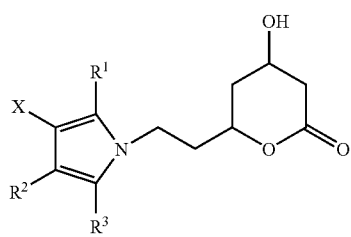

and e) subjecting the compound of formula (5) when W represents =O, or compound of formula (6) to ring-opening, and removal of any remaining protecting groups, to give a compound of formula (7) or salts thereof:

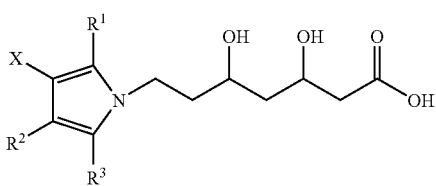

More preferably $R^1$ is an isopropyl group, $R^2$ is a phenyl group, $R^3$ is a 4-fluorophenyl group and X is a —$CO_2Me$, —$CO_2Et$ or —CONHPh group.

Protecting groups which may be represented by $P^1$ and $P^2$ include alcohol protecting groups, examples of which are well known in the art. Particular examples include tetrahydropyranyl groups. Preferred protecting groups are silyl groups, for example triaryl- and especially trialkylsilyl groups, and hydrocarbyl groups. Especially preferred are benzyl, methyl, trimethylsilyl, t-butyldimethylsilyl and t-butyldiphenylsilyl groups.

Protecting groups which may be represented by $P^1$ and $P^2$ may be the same or different. When the protecting groups $P^1$ and $P^2$ are different, advantageously this may allow for the selective removal of only $P^1$ or $P^2$. Preferably, when the protecting groups $P^1$ and $P^2$ are different, $P^1$ is a benzyl or silyl group and $P^2$ is a methyl group.

Cyanation of compounds of formula (1) can be achieved by methods known in the art for displacing a halo group with a cyanide. Preferably, the process comprises contacting the compound of formula (1) with a source of cyanide. Preferred sources of cyanide include cyanide salts, especially ammonium or alkali metal cyanides, particularly sodium or potassium cyanide. A particularly preferred process comprises contacting the compound of formula (1) with 5 molar equivalents of KCN in the presence of dimethylsulfoxide solvent at a temperature of, for example, from 50 to 120° C. preferably from 60 to 100° C. and more preferably from 70 to 90° C., typically about 80° C.

Reduction of compounds of formula (2) can be achieved using reduction systems known in the art for the reduction of nitrile groups. Preferred reductions systems include reduction with Raney nickel and hydrogen, reduction with hydrogen in the presence of a catalyst, such as palladium on carbon, reduction using hydride reagents, such as LiAlH4. Most preferred is reduction using boranes such as borane-THF. When palladium on carbon catalysed hydrogenation is employed, preferred conditions comprise the use of methanol solvent at elevated temperature, such as about 40° C., in the presence of from about 0.01 to 100 molar equivalents of ammonia.

The coupling of the compound of formula (3) with the compound of formula (4) may employ conditions analogous to those given in WO89/07598 for the corresponding coupling. The conditions preferably comprise refluxing the compounds of formula (3) and (4) in a hydrocarbon solvent, such as toluene or cyclohexane, or mixtures thereof, followed by contact with aqueous acid, such as aqueous HCl.

When W represents $OP^2$, the protecting group may be removed to form a hydroxy group by methods known in the art for the removal of the given protecting group. For example, silyl protecting groups may be removed by contact with a source of fluoride ion, such as tetrabutylammonium fluoride, and benzyl groups may be removed by hydrogenolysis, such as reaction with hydrogen in the presence of palladium on carbon.

Oxidation of compounds formed by deprotection of compounds wherein W represents —$OP^2$ may employ conditions known in the art for the oxidation of pyranols to pyranones, and include those given in "Comprehensive Organic Transformations", R. C. Larock, $2^{nd}$ Ed (1999) p 1670, published by Wiley VCH, incorporated herein by reference. Preferred oxidation systems include $Ag_2CO_3$/Celite, especially Celite J2 (with Ag2CO3), bromine, Swern oxidation or Dess-Martin periodinane oxidation.

Ring opening of the compounds of formula (5), when W represent =O or formula (6) may employ conditions known in the art for ring opening of a pyranone. Preferably, the ring is opened by contact with a base, such as sodium hydroxide. Methanol is conveniently employed as solvent.

Remaining protecting groups may be removed by methods known in the art for the removal of the given protecting group. For example, silyl protecting groups may be removed by contact with a source of fluoride ion, such as tetrabutylammonium fluoride, benzyl ethers may be removed by hydrogenolysis, and methyl acetals may be removed by treatment with dilute aqueous acid.

It will be recognised that when X represents a group of formula —$COOR^4$, this may be converted to a group wherein X represents —$CONR^5R^6$ at any stage during the process, for example by reaction of the corresponding compounds of formulae (4), (5), (6) or (7) with a compound of formula HNR⁵R⁶.

It will also be recognised that compounds of formulae (2) and (3) may also be subjected to oxidation (when W represents —OH) or deprotection and oxidation (when W represents (—O-protecting group) to form the corresponding compound wherein W represents =O.

Preferred compounds of formula (1) are compounds of formula:

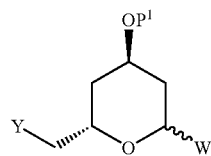

wherein W, $P^1$ and Y are as previously described.

Preferred compounds of formula (2) are compounds of formula:

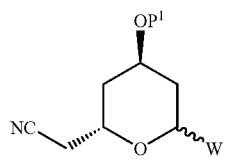

wherein W and $P^1$ are as previously described.

Preferred compounds of formula (3) are compounds of formula:

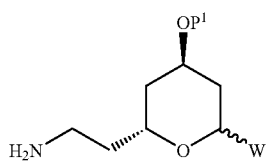

wherein W and $P^1$ are as previously described.

Preferred compounds of formula (5) are of formula:

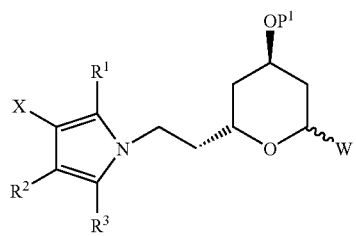

wherein $R^1$, $R^2$, $R^3$, W, X and $P^1$ are as previously described.

Preferred compounds of formula (6) are of formula:

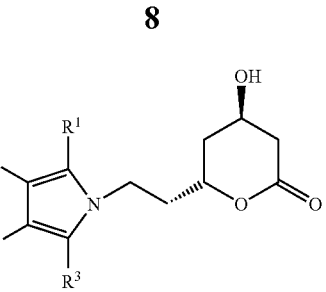

wherein $R^1$, $R^2$, $R^3$, and X are as previously described.

Preferred compounds of formula (7) are of formula:

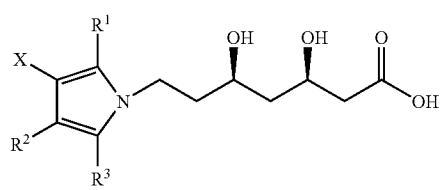

wherein $R^1$, $R^2$, $R^3$, and X are as previously described.

Compounds of formula (7) are advantageously converted to pharmaceutically acceptable salts, especially their calcium salts.

Compounds of formula (4) are advantageously prepared by the methods given in J. Med. Chem., 1991, 34, pp 357-366. Particularly preferred compounds of formula (4) are compounds of formula:

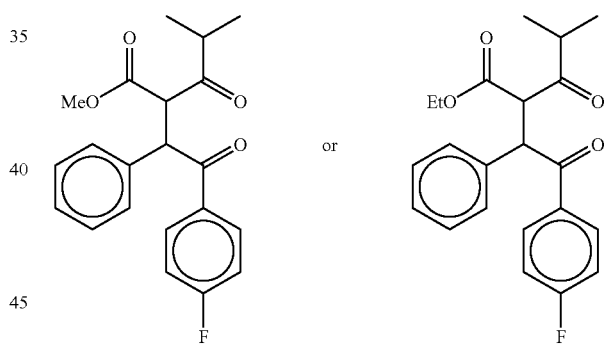

Compounds of formula (1) are advantageously prepared by enzyme catalysed condensation of acetaldehyde and 2-haloacetaldehyde, for example using the method given in U.S. Pat. No. 5,795,749.

Compounds of formulae (2) and (3) and, when W is $OP^2$, formula (5) form further aspects of the present invention.

In preferred Compounds of formula (2) and (3) $P^1$ is a protecting group and preferably W represents —$OP^2$. When $P^1$ is a protecting group and W represents —$OP^2$, preferably $P^1$ and $P^2$ are different.

More preferred compounds of formula (2) and (3) are compounds where $P^1$ is a benzyl or silyl group and W represents $OP^2$ where $P^2$ is a methyl group.

Preferred compounds of formula (5) are compounds where $P^1$ is hydrogen, benzyl or silyl group and W represents =O or $OP^2$ where $P^2$ is a methyl group.

More preferred compounds of formula (5) are compounds where $R^1$ is a $C_{1-6}$ alkyl group, $R^2$ is an aryl group, $R^3$ is an aryl group, X is COZ where Z is $OR^4$ where $R^4$ is an alkyl group or Z is $NR^5R^6$ where and $R^5$ and $R^6$ each independently is hydrogen alkyl or aryl, $P^1$ is hydrogen, benzyl or silyl group and W represents =O or $OP^2$ where $P^2$ is a methyl group.

Most preferred compounds of formula (5) are compounds where $R^1$ is an isopropyl group, $R^2$ is a phenyl group, $R^3$ is 4-fluorophenyl aryl group, X is COZ where Z is $OR^4$ where $R^4$ is a methyl or ethyl group or Z is $NR^5R^6$ where and $R^5$ is hydrogen and $R^6$ phenyl, $P^1$ is hydrogen, benzyl or silyl group and W represents =O or $OP^2$ where $P^2$ is a methyl group.

The invention is illustrated by the following Examples.

EXAMPLE 1

Preparation of Chlorolactol methyl acetal ((2S,4R)-2-(chloromethyl)-6-methoxytetrahydro-2H-pyran-4-ol), a Compound of Formula 1 Where Y=Cl, $P^1$=H and W=—$OP^2$, in Which $P^2$=Me Crude chlorolactol (15 g) was dissolved in methanol (150 ml) and heated to 40° C. for 2 hours in the presence of 0.1 ml sulphuric acid. The solvent was removed by rotary evaporation to afford the product as a dark brown flowing oil. The product was dissolved in DCM and washed with sodium bicarbonate solution. The solvent was removed by rotary evaporation to afford the product as a dark brown flowing oil, which was purified by column chromatography (16.1 g) m/z 179, 149 and 113; $^1$H nmr $CDCl_3$ 3.6-3.7 (m 2H), 4.1 (m 1H), 1.5-1.6 (m 2H), 4.0 (m 1H), 1.3-1.6 (m 2H), 4.9 (m 1H), 3.3 & 3.5 (s 3H); $^{13}$C nmr $CDCl_3$ 32, 36, 45, 55&56, 64, 65, 94.

EXAMPLE 2

Preparation of O-benzyl-chlorolactol methyl acetal ((2S,4R)-4-(benzyloxy)-2-(chloromethyl)-6-methoxytetrahydro-2H-pyran), a Compound of Formula 1 Where Y=Cl, $P^1$=Bz and W=—$OP^2$, in Which $P^2$=Me Chlorolactol methyl acetal (1 g) was dissolved in THF (5 ml) and charged to sodium hydride (0.33 g 60% in mineral oil) in THF (5 ml) at room temperature. Benzyl bromide (1.9 g) was added dropwise and the mass heated to 80° C. for 2 hours. Methanol (2 ml) was added and the mass was partitioned between DCM/water, and was then washed with water. The organic phase was dried and the solvent was removed by rotary evaporation to afford an orange flowing oil (2.1 g). m/z 270; 238; 203; 132; 91; $^1$H nmr $CDCl_3$ 1.6-2.0 (m 4H), 3.4 & 3.5 (s 3H), 3.6 (m 2H), 3.8 (m 1H), 4.0 (m 1H), 4.5 (m 2H), 4.7 (m 1H), 7.3-7.5 (m 5H); $^{13}$C nmr $CDCl_3$ 32&33, 46, 55&56, 58, 66, 74, 96&98, 128-131.

EXAMPLE 3

Preparation of Cyano-O-benzyl lactol methyl acetal ([(2R,4R)-4-(benzyloxy)-6-methoxytetrahydro-2H-pyran-2-yl]acetonitrile), a Compound of Formula 2 Where $P^1$=Bz and W=—$OP^2$, in Which $P^2$=Me O-benzyl-chlorolactol methyl acetal (5 g) was dissolved in DMSO (50 ml) containing Potassium cyanide (5 g) and heated for 4 days at 80° C. The mass was then partitioned between diethylether (50 ml) and water (50 ml). The organic phase was removed, dried and the solvent was removed by rotary evaporation to afford a dark oil, which was purified by column chromatography m/z 261, 229, 184, 123, 107, 91; $^1$H nmr $CDCl_3$ 1.6-1.9 (m 4H), 2.5 (m 2H), 3.4 & 3.5 (s 3H), 3.6 (m 1H), 3.8 (m 1H), 4.5 (s 2H); $^{13}$C nmr $CDCl_3$ 24, 34, 36, 54, 56, 58, 68, 73, 98&100, 117, 122-128.

EXAMPLE 4

Preparation of Aminoethyl-O-benzyl-lactol methyl acetal (2-[(2R,4R)-4-(benzyloxy)-6-methoxytetrahydro-2H-pyran-2-yl]ethanamine), a Compound of Formula 3 where $P^1$=Bz and W=—$OP^2$, in Which $P^2$=Me Borane-THF complex (1 molar solution) (1.19 mls) was charged to a nitrogen purged flask at 10° C. and diluted with THF (2.5 mls). Cyano-O-benzyl lactol methyl acetal (0.05 g) was dissolved into THF (7.5.5 mls) at 10° C. and charged to the borane. The resultant mixture was then heated at reflux for 9 hours. The mixture was cooled, quenched with methanol (10 ml) and concentrated in vacuo. A further two portions of Methanol (2×10 mls) were added, and the mixture twice concentrated to dryness. The final concentration afforded an oil (45 mg).

TLC ($CH_2Cl_2$): new spot at Rf=0.05, positive ninhydrin stain, no residual nitrile.

m/z 265, 233, 107, 91; $^1$H nmr $CDCl_3$ 1.6-1.9 (m, 6H), 3.4 & 3.45 (s, 3H), 3.5 (2H), 3.6 (m, 1H), 3.8 (m, 1H), 4.5 (s, 2H), 4.7 (m, 1H), 7.1 (m, 5H).

$^{13}$C nmr $CDCl_3$ 24, 26, 34, 36, 54, 56, 58, 68, 73, 98 & 100, 122-128.

EXAMPLE 5

Preparation of Pyrrole Ester O-benzyl lactol methyl acetal, a Compound of Formula 5 where $R^1$=iPr, $R^2$=Ph, $R^3$=4-$FC_6H_4$, X=$CO_2$Et, $P^1$=Bz and W=—$OP^2$, in Which $P^2$=Me Aminoethyl-O-benzyl-lactol methyl acetal (1.00 g) was dissolved in THF (10 ml). DiketoEster (1.12 g) was added, followed by acetic acid (2 ml) and the mixture heated to 80° C. for 2 days. After concentration in vacuo the reaction mass was partitioned between diethyl ether (10 ml) and water (10 ml). The organic phase was collected, dried ($MgSO_4$), and the solvent removed in vacuo to afford a brown oil which was purified by column chromatography (0.38 g). M/z: 599, 567, 460, 107, 91; $^1$H nmr $CDCl_3$ 1.15 (t, 3H), 1.3 (d, 6H), 1.6-1.9 (m, 6H), 3.4 & 3.45 (s, 3H), 3.5 (2H), 3.6 (m, 2H), 3.8 (m, 1H), 4.1 (q, 2H), 4.5 (s, 2H), 4.7 (m, 1H), 7.1 (m, 14H).

19F nmr: Shift from 106 ppm (DiKeto Ester) to 115 ppm (product).

EXAMPLE 6

Preparation of Pyrrole Anilide O-benzyl lactol methyl acetal, a Compound of Formula 5 where $R^1$=iPr, $R^2$=Ph, $R^3$=4-$FC_6H_4$, X=C(O)NHPh, $P^1$=Bz and W=—$OP^2$, in which $P^2$=Me Pyrrole Ester O-benzyl lactol methyl acetal (0.30 g) was dissolved in DMF (5 ml). Aniline (1.0 g) was added and the mixture heated to 80° C. for 18 hours. After cooling, and concentration in vacuo the reaction mass was partitioned between diethyl ether (5 ml) and water (5 ml). The organic phase was collected, washed further with water (5 ml), dried ($MgSO_4$), and the solvent removed in vacuo to afford a brown oil which was purified by column chromatography (0.26 g). M/z 646, 614, 507, 107, 91; $^1$H nmr $CDCl_3$ 1.3 (d, 6H), 1.6-1.9 (m, 6H), 3.4 & 3.45 (s, 3H), 3.5 (2H), 3.6 (m, 2H), 3.8 (m, 1H), 4.5 (s, 2H), 4.7 (m, 1H), 6.8 (br.s 1H), 7.1 (m, 19H).

EXAMPLE 7

Preparation of Pyrrole Anilide OH lactol methyl acetal (Lipitor Lactol-OMe) a Compound of Formula 5 where $R^1$=iPr, $R^2$=Ph, $R^3$=4-$FC_6H_4$, X=C(O)NHPh, $P^1$=H and W=—$OP^2$, in which $P^2$=Me Pyrrole Anilide O-benzyl lactol methyl acetal (0.15 g) was dissolved in Methanol (5 ml). 10% Pd/C (0.1 g) was added under Nitrogen. The system was flushed with Hydrogen, the heated under an atmosphere of hydrogen for 6 hours. After removal of the Pd/C by filtration, and concentration of the reaction mass in vacuo, the residual brown oil was purified by column chromatography. M/z 556, 524, 506; $^1H$ nmr $CDCl_3$ 1.3 (d, 6H), 1.6-1.9 (m, 6H), 3.4 & 3.45 (s, 3H), 3.5 (2H), 3.6 (m, 2H), 3.8 (m, 1H), 4.7 (m, 1H), 6.8 (br.s 1H), 7.1 (m, 14H).

EXAMPLE 8

Preparation of Pyrrole Anilide OH lactol (Lipitor Lactol), a Compound of Formula 5 where $R^1$=iPr, $R^2$=Ph, $R^3$=4-$FC_6H_4$, X=C(O)NHPh, $P^1$=H and W=—$OP^2$, in which $P^2$=H Pyrrole Anilide OH lactol methyl acetal (0.050 g) was dissolved in Methanol (2 ml), and water (2 ml) was added, followed by 0.1N HCl (1 ml). After stirring at room temperature for 2 hours, the mixture was concentrated in vacuo to afford the product as a colourless oil. M/z 542, 524, 506; $^1H$ nmr $CDCl_3$ 1.3 (d, 6H), 1.6-1.9 (m, 6H), 3.45 (2H), 3.6 (m, 2H), 3.8 (m, 1H), 5.0 (m, 1H), 6.8 (br.s 1H), 7.1 (m, 14H); $^{13}C$ nmr $CDCl_3$ 91.6 ppm (Lactol C); FTIR: 1652 $cm^{-1}$ (Amide)

EXAMPLE 9

Preparation of Lactone, a Compound of Formula 6 where $R^1$=iPr, $R^2$=Ph, $R^3$=4-$FC_6H_4$, X=C(O)NHPh, $P^1$=H The Pyrrole Anilide OH lactol (35 mg, 0.065 mmol) in dichloromethane (0.5 ml) was added to Dess-Martin periodinane (30 mg, 0.07 mmol) and stirred at room temperature for 2.5 hours. The reaction was partitioned between 1M sodium hydroxide and diethyl ether. The phases were then separated and the organic volume reduced in vaccuo to afford the crude product oil.

$^1H$ nmr 500 MHz $CDCl_3$: 9.8, 7.5, 7.28, 7.2, 7.08, 7.02, 6.98, 5.2, 4.5, 4.1, 4.0, 3.9, 3.2, 2.6, 2.4, 1.6, 1.4.

$^{13}C$ nmr 125.72 MHz DMSO: 169.6, 165.9, 139.3, 135.9, 134.7, 133.3, 129.4, 128.8, 128.4, 127.5, 127.2, 125.3, 122.9, 120.7, 119.3, 117.6, 115.4, 25.5, 22.1, 22.3, 39.5, 34.5, 72.8, 36.8, 61.0, 38.3.

EXAMPLE 10

Preparation of Atorvastatin (Hydrolysis of Lactone), a Compound of Formula 7 where $R^1$=iPr, $R^2$=Ph, $R^3$=4-FC6H4, X=C(O)NHPh The lactone (1.1 g) was dissolved in ethanol (10 ml). Water (2 ml) and $Ca(OH)_2$ (0.15 g) were added and the suspension warmed to 60° C. for 3 hours. A further 10 ml of warm water was added, then the mixture allowed to cool slowly to room temperature. The precipitate formed was filtered and dried to give atorvastatin calcium salt (0.3 g). The material was identical to an authentic sample by mixed melting point, NMR and mass spectrometry.

Independent Preparation of Pyrrole Anilide OH lactol (Lipitor Lactol), a Compound of Formula 5 Where $R^1$=iPr, $R^2$=Ph, $R^3$=4-$FC_6H_4$, X=C(O)NHPh, $P^1$=H and W=—$OP^2$, in Which $P^2$=H, from an Authentic Source of Lactone An authentic sample of Lactone (530 mg) was dissolved in anhydrous DMF (5 ml), followed by imidazole (174 mg), then TBDMS chloride (371 mg). The mixture was stirred at room temperature. After 6 hours, the reaction was worked up by addition of $Et_2O$ (30 ml) and water (30 ml). The separated organic phase was further washed with water (2×20 ml), dried, and concentrated in vacuo to afford silylated lactone as a white powder (470 mg, 73%).

The silylated lactone (233 mg) was dissolved in anhydrous dichloromethane (5 ml), then cooled to −78° C. under Nitrogen. DIBAL (0.31 ml, 1M in toluene) was added dropwise and the mixture stirred for 10 minutes at −78° C. The mixture was then quenched by addition of 1 ml of 10% aqueous Rochelle's salt and allowed to warm to room temperature. After addition of further dichloromethane (10 ml) and water (10 ml), the phases were separated and the organic phase dried and concentrated in vacuo. The residual oil was purified by column chromatography (50% $Et_2O$ in hexane). FTIR: 1668 $cm^{-1}$ (amide). Stretch at 1735 $cm^{-1}$ (Lactone) no longer present.

The silylated lactol (100 mg) was dissolved in anhydrous THF. HF.pyridine was added (0.1 ml) at 0° C. and allowed to warm to room temperature. The mass was quenched with ether/and sodium bicarbonate solution. The phases separated and the aqueous phase back extracted with ether. The organic phases were combined, dried and evaporated to produce and oil (75 mg). M/z 542, 524, 506; $^1H$ nmr $CDCl_3$ 1.3 (d, 6H), 1.6-1.9 (m, 6H), 3.45 (2H), 3.6 (m, 2H), 3.8 (m, 1H), 5.0 (m, 1H), 6.8 (br.s 1H), 7.1 (m, 14H); $^{13}C$ nmr $CDCl_3$ 91.6 ppm (Lactol C); FTIR: 1652 $cm^{-1}$ (Amide)

The invention claimed is:

1. A process for the preparation of a compound of formula (7) or a salt thereof:

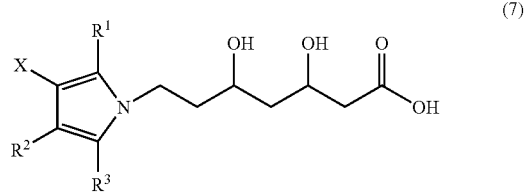

(7)

wherein
$R^1$ represents an alkyl group;
$R^2$ represents an aryl group;
$R^3$ represents an aryl group;
X represents a group of formula —COZ, wherein Z represents —$OR^4$, in which $R^4$ represents alkyl, or —$NR^5R^6$, wherein $R^5$ and $R^6$ each independently represent H, alkyl, or aryl;
which comprises
a) cyanating a compound of formula (1):

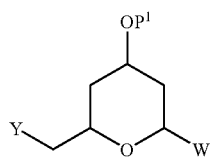

(1)

wherein Y represents a halo group; $P^1$ represents hydrogen or a protecting group, and W represents —$OP^2$, in which $P^2$ represents hydrogen or a protecting group, to give a compound of formula (2):

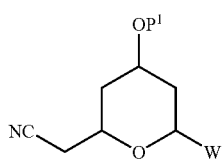

(2)

b) reducing the compound of formula (2) to give a compound of formula (3):

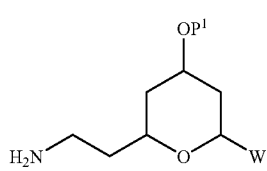

(3)

c) coupling the compound of formula (3) with a compound of formula (4):

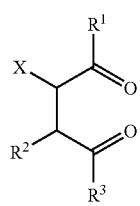

(4)

to give a compound of formula (5):

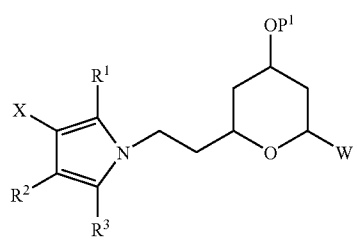

(5)

d) deprotecting and then oxidising the compound of formula (5) to give a compound of formula (6):

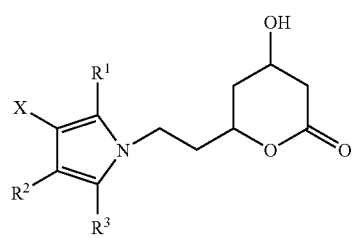

(6)

and e) subjecting the compound of formula (6) to ring-opening, and removal of any remaining protecting groups, to give a compound of formula (7) or a salt thereof:

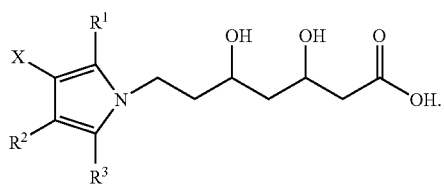

(7)

2. The process according to claim 1, wherein $R^1$ is an isopropyl group, $R^2$ is a phenyl group, $R^3$ is a 4-fluorophenyl group, and X is —$CO_2Me$, —$CO_2Et$ or —CONHPh.

3. The process of claim 1, wherein Y represents Cl or Br.

4. The process of claim 1, wherein $R^1$ represents a $C_{1-6}$ alkyl group.

5. The process of claim 1, wherein $R^1$ represents an isopropyl group.

6. The process of claim 1, wherein $R^2$ represents a phenyl group.

7. The process of claim 1, wherein $R^3$ represents a 4-fluorophenyl group.

8. The process of claim 1, wherein Z represents —$OR^4$, in which $R^4$ represents alkyl.

9. The process of claim 1, wherein Z represents —$OR^4$, in which $R^4$ represents a methyl or ethyl group.

10. The process of claim 1, wherein Z represents —$NR^5R^6$, wherein $R^5$ and $R^6$ each independently represent H, alkyl, or aryl.

11. The process of claim 1, wherein Z represents —$NR^5R^6$, wherein $R^5$ is H, and $R^6$ is phenyl.

12. The process of claim 1, wherein $R^1$ represents a $C_{1-6}$ alkyl group; and $R^2$ represents a phenyl group.

13. The process of claim 1, wherein $R^1$ represents a $C_{1-6}$ alkyl group; $R^2$ represents a phenyl group; and $R^3$ represents a 4-fluorophenyl group.

14. The process of claim 1, wherein $R^1$ represents a $C_{1-6}$ alkyl group; $R^2$ represents a phenyl group; $R^3$ represents a 4-fluorophenyl group; and Z represents —$OR^4$, in which $R^4$ represents a methyl or ethyl group.

15. The process of claim 1, wherein $R^1$ represents a $C_{1-6}$ alkyl group; $R^2$ represents a phenyl group; $R^3$ represents a 4-fluorophenyl group; and Z represents —$NR^5R^6$, wherein $R^5$ is H, and $R^6$ is phenyl.

* * * * *